United States Patent
Ishii et al.

(10) Patent No.: US 12,303,248 B2
(45) Date of Patent: May 20, 2025

(54) MAGNETIC RESONANCE IMAGING APPARATUS AND SIGNAL PROCESSING METHOD

(71) Applicant: FUJIFILM Healthcare Corporation, Kashiwa (JP)

(72) Inventors: Koki Ishii, Chiba (JP); Atsushi Ota, Chiba (JP); Takashi Chuman, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 197 days.

(21) Appl. No.: 18/201,069

(22) Filed: May 23, 2023

(65) Prior Publication Data

US 2023/0397834 A1    Dec. 14, 2023

(30) Foreign Application Priority Data

Jun. 13, 2022  (JP) .................................. 2022-95149

(51) Int. Cl.
*A61B 5/055* (2006.01)
*A61B 5/00* (2006.01)

(52) U.S. Cl.
CPC ................ *A61B 5/055* (2013.01); *A61B 5/72* (2013.01); *A61B 5/002* (2013.01)

(58) Field of Classification Search
CPC ............ A61B 5/055; A61B 5/72; A61B 5/002
See application file for complete search history.

(56) References Cited

U.S. PATENT DOCUMENTS 7,173,427 B1 * 2/2007 Adachi .............. G01R 33/3621 324/318

FOREIGN PATENT DOCUMENTS

JP        2001087243 A  *  4/2001
JP        2005-270583 A     10/2005

OTHER PUBLICATIONS

English translation of JP-2001-087243 (Year: 2001).*
R. Behin et al., "Dynamic Range Requirements for MRI", Conc. Magn. Reson., vol. 26B(1), pp. 28-35 (2005).

* cited by examiner

*Primary Examiner* — G. M. A Hyder
(74) *Attorney, Agent, or Firm* — Paul Teng

(57) ABSTRACT

In an MRI apparatus, a dynamic range of an MR signal is extended without increasing the time for imaging nor manufacturing cost. The MRI apparatus is provided with a receiver 200 configured to perform the A/D conversion on two-system nuclear magnetic resonance signals according to a direct sampling method. The receiver 200 comprises a distributor 201 configured to divide each of the nuclear magnetic resonance signals into two-system signals, an attenuator 202 configured to attenuate an overflowed signal outputted from the distributor, and a switch 203 configured to switch between the signals having the same gain to output the switched signal. Also provided is a digital processing means having ADCs of the same number as that of the nuclear magnetic resonance signals to perform the AD conversion respectively for the two types of signals, restore the attenuated signals, and recombine the signals. After switching, the signals outputted with different gains are combined to increase the number of bits of digital data with respect to all the sampling points, thereby extending the dynamic range.

10 Claims, 13 Drawing Sheets

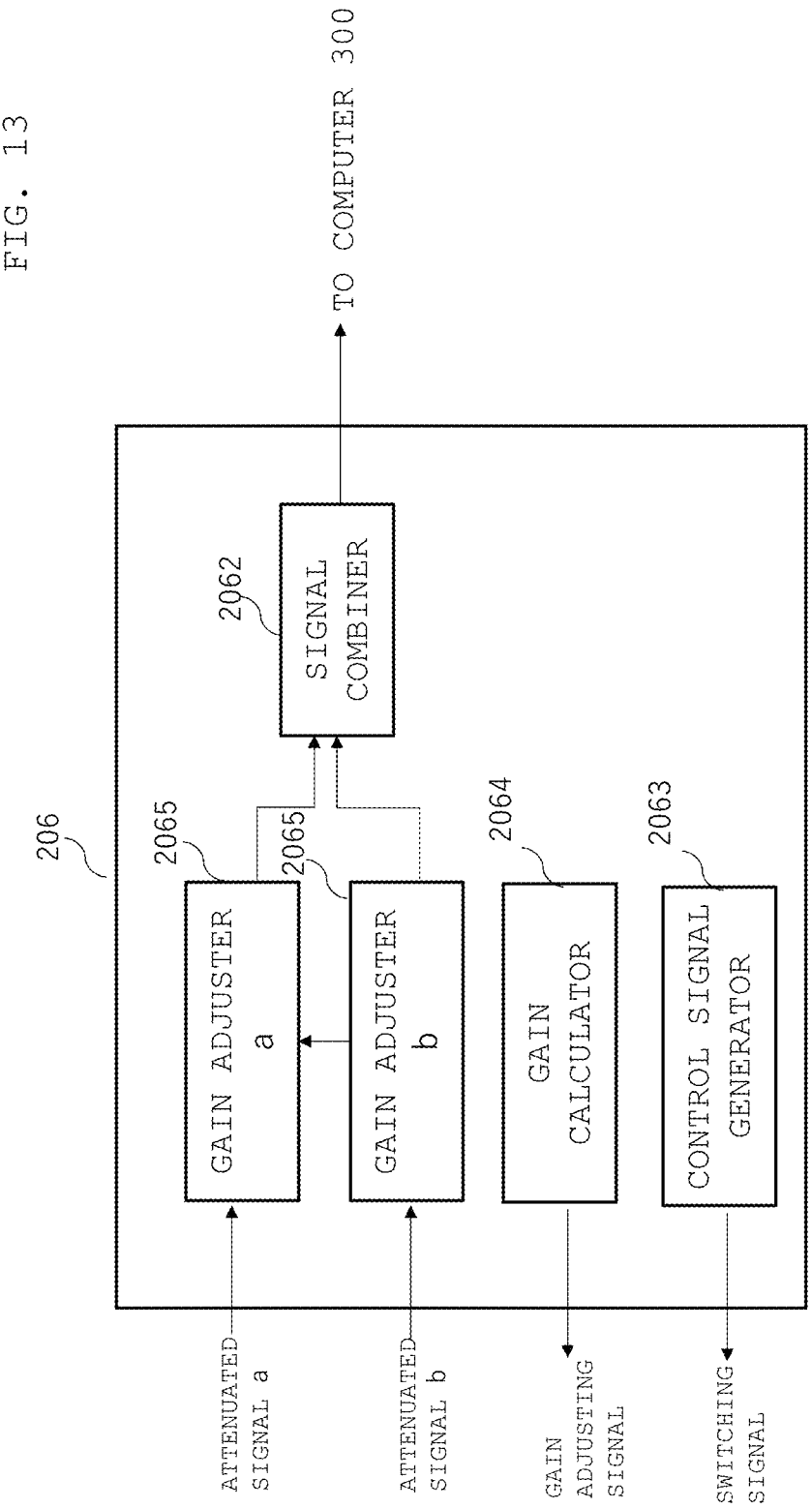

MAGNETIC RESONANCE IMAGING APPARATUS AND SIGNAL PROCESSING METHOD

BACKGROUND OF THE INVENTION

Technical Field

The present invention relates to a magnetic resonance imaging apparatus and an imaging method to have a wide dynamic range.

Description of the Related Art

In recent years, magnetic resonance imaging (MRI) technologies have made remarkable progress, including sensitivity enhancement of receive coils for improving an image quality and imaging speed, and introduction of image processing techniques including diversification of an imaging sequence and utilization of machine learning such as deep learning. Magnetic resonance signals (MR signals, hereinafter also referred to as echo signals) detected by the receive coils of MRI are subjected to appropriate signal processing, and thereafter subjected to A/D (analog-to-digital) conversion and image processing.

As shown in FIG. 3, since MRI is a signal measurement in Fourier space, the MR signal has characteristics that the signal intensity is very high in the center portion of the Fourier space, but is very low in the surroundings (regions where the spatial frequency is high). In addition, a mode of the MR signal is related to an imaging method, i.e., what kind of images are taken under which imaging sequence, and it is necessary to consider that a dynamic range becomes extremely large in an MRI apparatus.

Further in recent years, static magnetic field strength is increased and SNR (Signal-to-Noise-Ratio) of a 3D imaging method is made higher, and thus it is required to have a high-speed and high-resolution A/D converter (hereinafter, referred to as ADC) in order to achieve accurate digitization. However, the currently available ADCs are not always satisfactory in terms of quantization resolution, sampling rate, and price of the converter.

In order to cope with the problems above, "Dynamic Range Requirements for MRI, R. Bein, J. Bishop, R. H. Henkelman, Conc. Magn. Reason. B26: 28-2005" (hereinafter, referred to as Non-Patent Literature 1) discloses a method (Dual Scan method) for acquiring data twice with changing the difference in gains, and this method is widely adopted in the technical field of MRI imaging.

In addition, Japanese Unexamined Patent Application Publication No. 2005-270583 (FIG. 7 and a corresponding part of the embodiment) (hereinafter, referred to as Patent Literature 1) suggests a method in which two types of amplitude-adjusted signals are obtained; one is a first amplitude-adjusted signal obtained by adjusting the amplitude of an MR signal by a first amplitude adjuster, and the other is a signal obtained by adjusting the amplitude of a difference signal by a second amplitude adjuster, the difference between the original MR signal and the first amplitude-adjusted signal. Then, each of the obtained two types of signals is subjected to the A/D conversion (analog-to-digital conversion) and combined by a digital processor for pseudo-extension of the dynamic range.

SUMMARY OF THE INVENTION

Technical Problem

The Dual Scan method disclosed by Non-Patent Literature 1 is not preferable in terms of stability of the apparatus because the imaging is performed twice. In particular, MRI imaging is performed for a long period of time, the conditions of the first imaging and the second imaging do not always coincide with each other, and therefore, combining signals is not simple. Thus, there are disadvantages that artifacts are likely to be generated in the image and also the imaging time tends to be longer.

In addition, in the method disclosed in Patent Literature 1, when signals from a plurality of channels are processed, the ADCs corresponding to the number of channels are required, and as the number of channels increases, a large number of ADCs are required. This leads to a complicated apparatus and increase of manufacturing cost.

The present invention has been made in view of the above-described conventional issues, and an object of the present invention is to eliminate increasing of the size of the apparatus and manufacturing cost, and to extend the dynamic range with respect to all sampling points of the MR signal.

Solution to Problem

In order to achieve the above-described object, the present invention divides an MR signal into signals of two or more systems, and provides a first ADC configured to process the signal of one system as it is, and a second ADC configured to process the signal of the other system after gain adjustment. Then, with respect to multiple MR signals inputted to a receiver, switching is performed on the timing of inputs to the first ADC and to the second ADC, and on the timing of combining the output from the first ADC with the output from the second ADC after the gain adjustment. With this configuration, it is possible to perform the AD conversion with a virtually extended dynamic range, with respect to each of multiple MR signals, using only two types of ADCs having different gains.

An MRI apparatus of the present invention comprises a magnetic field generator configured to generate nuclear magnetic resonance in a subject, a receiver having a receive coil configured to receive a nuclear magnetic resonance signal emitted from the subject, and an arithmetic unit configured to perform a process including image reconstruction using the nuclear magnetic resonance signals received by the receiver. The receiver comprises a distributor configured to divide the nuclear magnetic resonance signal into at least two-system signals; a first-system signal and a second-system signal, a gain adjuster configured to perform gain adjustment on at least one of the first-system signal and the second-system signal, a first AD converter configured to perform analog-to-digital conversion on the first-system signal and a second AD converter configured to perform analog-to-digital conversion on the second-system signal, the first-system signal and the second-system signal having been adjusted by the gain adjuster to have different gains, and a digital processor configured to restore the gain of the digitized signal after adjusted by the gain adjuster to an original gain, and to combine the digitized two-system signals. The digital processor further comprises a control unit configured to control inputs to the first AD converter and the second AD converter, and the outputs from the first AD converter and the second AD converter.

A signal processing method of the present invention is provided for processing a nuclear magnetic resonance signal measured by an MRI apparatus, and the method comprises dividing the nuclear magnetic resonance signal into two-system signals; a first-system signal and a second-system signal, performing analog-to-digital conversion on the first-system signal as it is or after gain adjustment, performing analog-to-digital conversion on the second-system signal after the gain adjustment to have a gain different from that of the first-system signal, and after restoring the adjusted gain to an original gain, combining the digitized first-system signal with the digitized second-system signal. At this time, the signal processing method controls switching the analog-to-digital conversion in response to the number of nuclear magnetic resonance signals to be processed, along with synchronizing the timing of the analog-to-digital conversion of the first-system signal with the timing of the analog-to-digital conversion of the second-system signal, with respect to one nuclear magnetic resonance signal.

According to the present invention, each of the nuclear magnetic resonance signals is divided into two-system signals, the signals in the respective systems having gains different from each other, and the signals having the same gain are sent (outputted) to either of the two ADCs, while switching is performed between the signals having the same gain. Then, the outputted signals having different gains, the signals being outputted in a switchable manner, are combined, whereby the number of bits of the digital data is increased with respect to all the sampling points. Accordingly, even if the number of signals to be processed increases, it is not necessary to increase the size of the apparatus nor increase the manufacturing cost associated therewith, and further, it is possible to extend the dynamic range without increasing the imaging time, enabling collection of high-definition image data.

BRIEF DESCRIPTION OF THE DRAWINGS

FIG. 13 is a functional block diagram showing the processing circuit according to the second embodiment.

DETAILED DESCRIPTION OF THE PREFERRED EMBODIMENTS

There will now be described embodiments of the present invention with reference to the accompanying drawings.

First Embodiment

First, an outline of an MRI apparatus to which the present invention is applied will be described.

Figure 1:
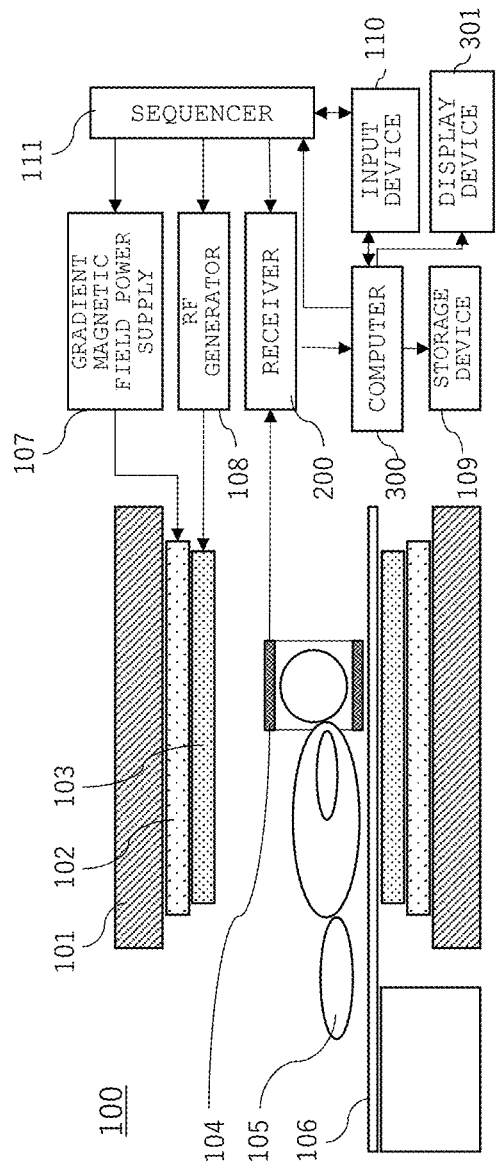
FIG. 1 is a block diagram showing the entire configuration of an MRI apparatus according to an embodiment of the present invention.

As illustrated in FIG. 1, an MRI apparatus 100 comprises a static magnetic field generator 101 configured to generate a static magnetic field in an imaging space placing an imaging site of a subject 105 on a table 106, a gradient magnetic field coil 102 configured to apply a gradient magnetic field to the imaging space, a transmission coil 103 configured to irradiate the subject 105 with an RF magnetic field pulse, and a receive coil 104 configured to receive an MR signal from the subject 105.

The MRI apparatus 100 further comprises a sequencer 111 configured to control the operation of a gradient magnetic field power supply 107, an RF generator 108, and a receiver 200 in accordance with a predetermined pulse sequence, a computer 300 configured to perform control of imaging via the sequencer 111, calculation using MR signals, and so on, an input device 110 configured to serve as an interface between the apparatus and a user, a display device 301, and a storage device 109 configured to store data required for imaging, images, and others.

The gradient power supply 107 drives the gradient coil 102 to apply gradient magnetic fields of three axes (X, Y, and Z) orthogonal to the static magnetic field. The transmission coil 103 is supplied with RF signals generated from the RF generator 108, and then irradiates the subject 105 with RF magnetic field pulses. MR signals received by the receiver 104 are transmitted to the receiver 200. The receiver 200 performs required signal processing such as the A/D conversion on the MR signals, and passes the resultant signals to the computer 300.

The sequencer 111 operates the gradient power supply 107, the RF generator 108, and the receiver 200 in accordance with a series of pulse-sequence information supplied from the input device 110 and the computer 300, and then collects the MR signals. There are various types of pulse sequences depending on how imaging is performed, and they are stored in the storage device 109 in advance.

The user enters control information of the MRI apparatus and sequence information related to the imaging via the input device 110, and then the computer 300 and the sequencer 111 are operated based on the entered information, allowing the user to acquire a desired image.

The computer 300 comprises a memory, a CPU, a GPU, and others, to receive digital signals from the receiver 200, performs an inverse Fourier transform on the collected data to reconstruct an image. The reconstructed image is stored in the storage device 109 and displayed on the display device 301 as appropriate.

Figure 2:
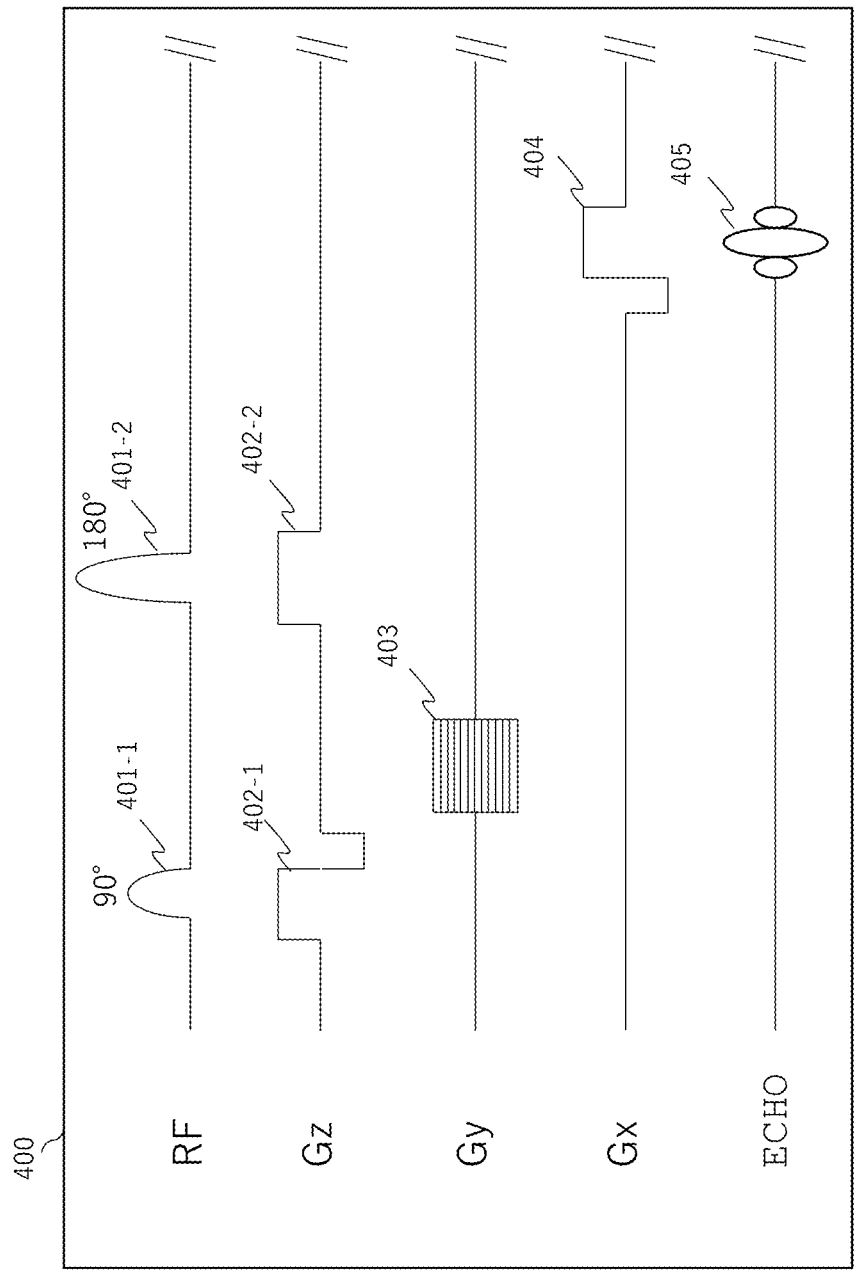
FIG. 2 illustrates an example of an imaging pulse sequence.

As shown in FIG. 2, for example, in the case where the imaging pulse sequence is a spin echo sequence 400, imaging by the MRI apparatus having the aforementioned configuration is performed as follows. The sequencer 111 transmits the RF magnetic field pulse (RF) 401-1 from the transmission coil 103 along with applying the slice-encoding gradient magnetic field (Gz) 402-1 from the gradient magnetic field coil 102, and then excites spins of the subject 105. Then, after applying the phase encoding gradient magnetic field (Gy) 403, the RF magnetic field pulse (180° pulse) 401-2 for reversing the magnetization is applied together with the slice encoding gradient magnetic field 402-2, after lapse of a predetermined time (TE/2) from the time of applying the RF magnetic field pulse for excitation (90° pulse), and the receive coil 104 receives the echo signal 405 with a peak maximized in the echo time (TE), along with applying the readout gradient magnetic field (Gx) 404. From applying the 90° pulse to receiving the echo signal is repeated at a predetermined repetition time TR with varying the strength of the phase encoding gradient magnetic field, and collects the echo signals the number of which is required for reconstructing the image.

Figure 3:
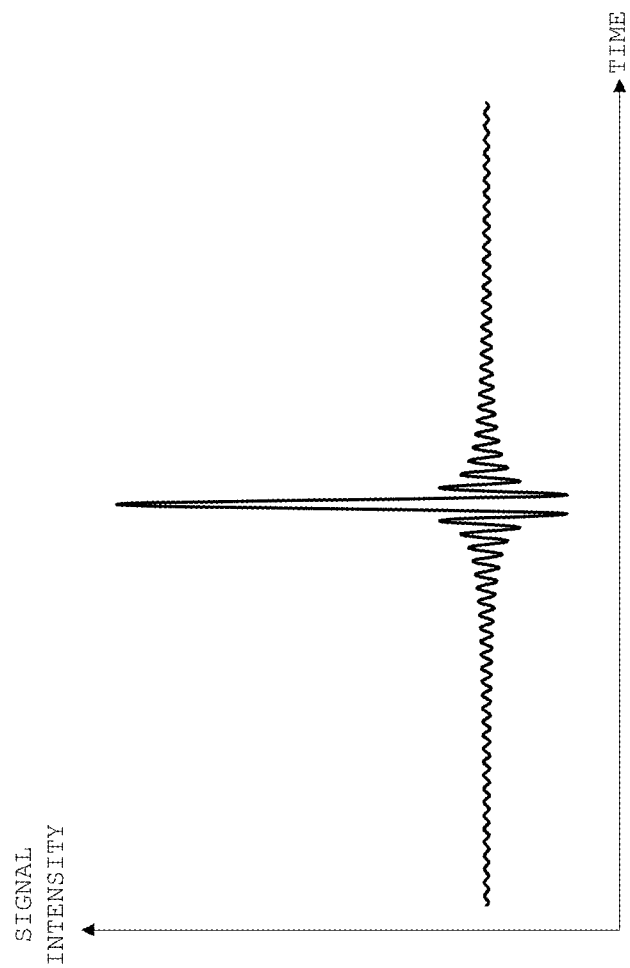
FIG. 3 illustrates a typical echo signal generated from a subject.

Here, as shown in FIG. 3 by way of example, the waveform of the received signal outputted from the receive coil 104 increases sharply toward the maximum peak, and then decreases, although there are fine fluctuations in amplitude (signal intensity). The amplitude at the position indicating the maximum peak is significantly different from the amplitude at the position indicating the minimum, and that the ratio therebetween is high (a dynamic range is large) is characteristic of an MR signal.

The receiver 200 performs sampling of the echo signal received by the receive coil 104 at a predetermined sampling period, thereby converting the amplitude (signal intensity) at the point of sampling time into a digital signal by an ADC. In order to process the MR signals having such large dynamic range, a high-performance ADC is required to handle the MR signals. The MRI apparatus of the present embodiment performs switching control on the ADC that has a common dynamic range, and is capable of managing the signal processing having a wide dynamic range.

There will now be described a specific configuration and operation of the receiver 200. In the following description, for the sake of simplicity, there will be described the case where two received signals are processed. The two signals indicate the following cases, for example; in one case, when the receive coil comprises two small coils (referred to as channels), the signals are respectively received by the two channels. In another case, the signal is a complex signal received by the receive coil serving as QD (quadrature) receiver, and the real part and the imaginary part of the complex signal are to be processed as the two signals.

Figure 4:
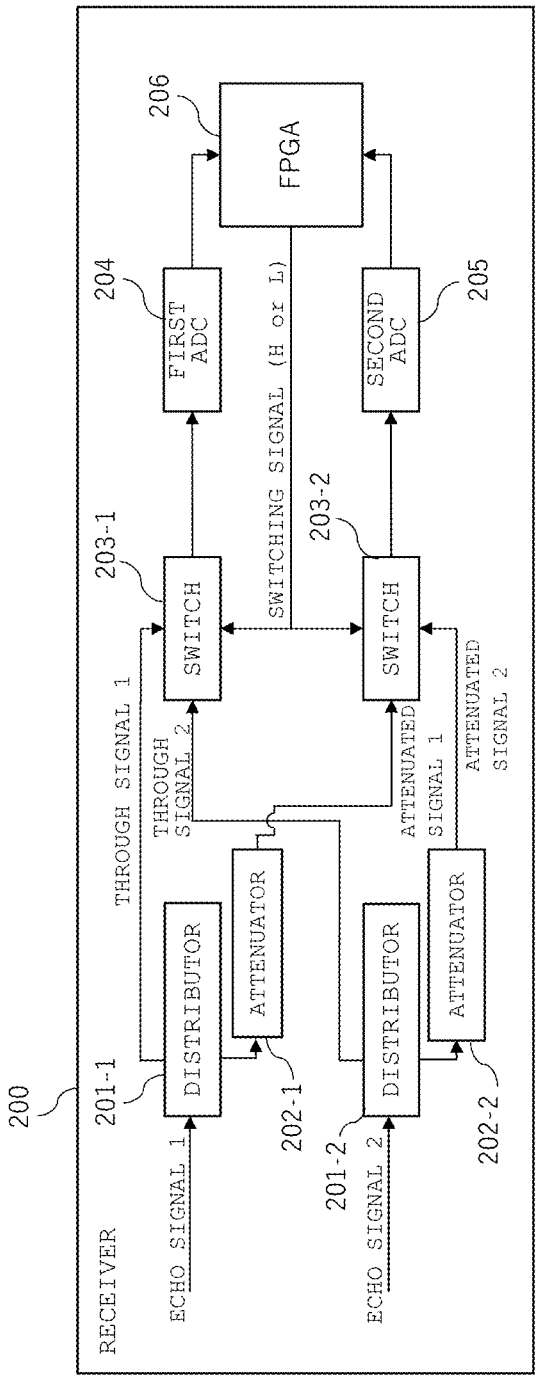
FIG. 4 illustrates a configuration of a receiver according to a first embodiment of the present invention.

As shown in FIG. 4, the receiver 200 of the present embodiment includes two distributors 201-1 and 201-2 provided to handle the two input signals (echo signal 1 and echo signal 2), attenuators 202-1 and 202-2 respectively connected to the outputs from the distributors 201-1 and 201-2, two ADCs (the first ADC 204 and the second ADC 205), switches 203-1 and 203-2 for switching signals to be inputted to the first ADC 204 and the second ADC 205, respectively, and a digital processing circuit (hereinafter, simply referred to as a processing circuit) 206.

The distributors 201-1 and 201-2 may be collectively referred to as a distributor 201, and the attenuators 202-1 and 202-2 may be collectively referred to as an attenuator 202, when there is no need of distinguishment between the two signals to be handled.

The distributor 201 divides each of the input echo signals (echo signal 1 and echo signal 2) into two-system signals. One of the outputs from the distributor 201 is directly inputted into the switch 203-1, and the other output is inputted into the switch 203-2 after attenuated by the attenuator 202. A signal inputted into the switch 203-1 is referred to as a through signal, and a signal inputted into the switch 203-2 after attenuated is referred to as an attenuated signal. The switches 203-1 and 203-2 may be collectively referred to as a switch 203 when there is no distinguishment between the through signal and the attenuated signal as the signals to be handled.

The switch 203-1 operates according to a control signal (switching signal) from the processing circuit 206, switching between the through signal 1 of the echo signal 1 and the through signal 2 of the echo signal 2, and sends (inputs) the switched signal to the first ADC 204. Similarly, the switch 203-2 switches between the attenuated signal 1 of the echo signal 1 and the attenuated signal 2 of the echo signal 2, and sends (inputs) the switched signal to the second ADC 205.

As the switch 203, there is employed a switch having a high switching rate, considering a transient response with respect to the sampling rates of the first ADC 204 and the second ADC 205, for example, a switch having a rise time of approximately half of the sampling period. Examples include but not limited to the followings; when the sampling frequency 100 MHz is used, the sampling period is 10 ns. Thus, it is possible to use the switch having the rise time of the post-switching signal, approximately 5 ns, which is half of the sampling period. With this configuration, when the processing circuit 206 combines two-system data items in the subsequent step, the data items can be combined without impairing data continuity in each system.

The processing circuit 206 is a digital processor that restores the dynamic range of the attenuated signal after the A/D conversion, then combines this restored signal with the through signal after the A/D conversion, thereby virtually extending the dynamic range, and also functions as a control unit configured to generate a control signal (switching signal) for controlling the switching. FIG. 4 illustrates the case where the processing circuit 206 is an FPGA (Field Programable Gate Array), but the processing circuit 206 is not limited to the FPGA, and other devices such as a programmable IC, a digital-signal processor (DSP), and a computer, may also be employed as the processing circuit.

Figure 5:
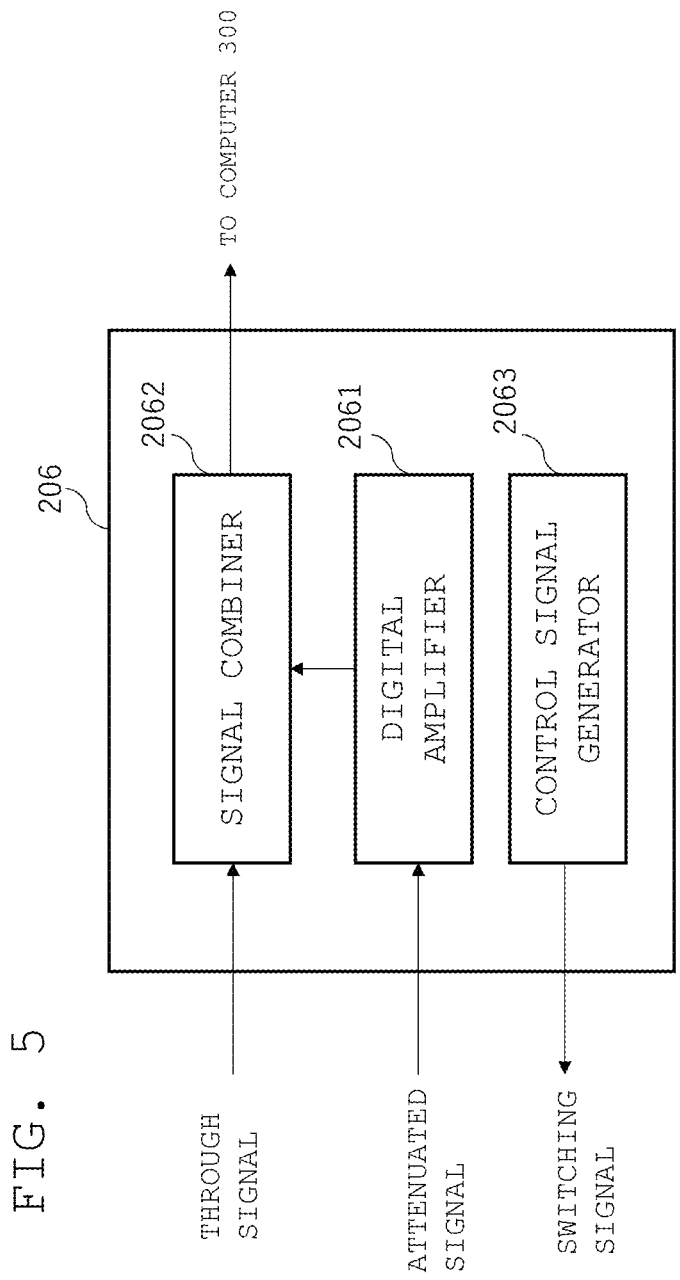
FIG. 5 is a functional block diagram showing a processing circuit according to the first embodiment.

FIG. 5 is a block diagram showing the function of the processing circuit 206. As illustrated, the processing circuit 206 includes a digital amplifier 2061, a signal combiner 2062, and a control signal generator 2063. The digital amplifier 2061 extends the dynamic range of the digitized attenuated signal to restore the original dynamic range. The signal combiner 2062 combines the through signal after the A/D conversion with the signal after extending the dynamic range of the attenuated signal. The combined signal is transmitted to the computer 300 and subjected to image reconstruction and other operations. The control signal generator 2063 generates a switching signal that determines the timing when the switch 203 switches between the inputs to the first ADC 204 and between the inputs to the second ADC 205.

Next, there will now be described the operation of the receiver 200 having the above-described configuration.

When the two signals, namely, the echo signal 1 and the echo signal 2, are inputted to the receiver 200, the distributor 201 divides each of the echo signals into two-system signals. The through signal 1 of the echo signal 1, which is one output from the distributors 201-1, and the through signal 2 of the echo signal 2, which is one output from the distributors 201-2, are both inputted into the switch 203-1, switched therein, and inputted to the first ADC 204. Further, the other output of the distributor 201-1 and the other output of the distributor 201-2 are subjected to a predetermined gain adjustment respectively in the attenuators 202-1 and 202-2, and become the attenuated signal 1 and the attenuated signal 2, with the dynamic range being lowered, and they are inputted to the switch 203-2, switched therein, and inputted to the second ADC 205.

Figure 6:
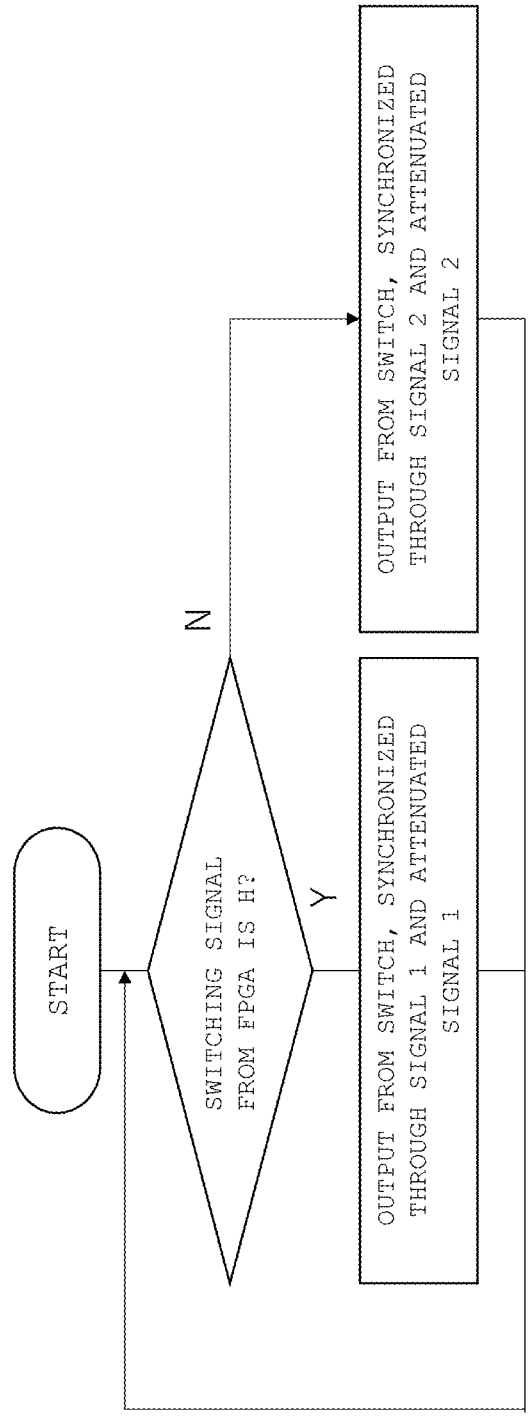
FIG. 6 is a flowchart showing the operation of a switch according to the first embodiment.

A switching signal generated by the control signal generator 2063 of the processing circuit (FPGA) 206 switches the outputs respectively from the switches 203-1 and 203-2, i.e., switching between the through signals and switching between the attenuated signals. For example, as shown in FIG. 6, when the switching signal is H, the switch 203-1 inputs the through signal 1 to the first ADC 204, and the switch 203-2 inputs the attenuated signal 1 to the second ADC 205. On the other hand, when the switching signal is L, the switch 203-1 inputs the through signal 2 to the first ADC 204, and the switch 203-2 inputs the attenuated signal 2 to the second ADC 205.

As shown in FIG. 4, the first ADC 204 subjects the switched output of the through signal to the A/D conversion, and the second ADC 205 subjects the switched output of the attenuated signal, attenuated by the attenuator 202, to the A/D conversion. Then, the respective digitized data items are outputted to the processing circuit 206. With this configuration, the processing circuit 206 receives alternately, the synchronized two-system digital signals of the echo signal 1, and the synchronized two-system digital signals of the echo signal 2.

Figure 7:
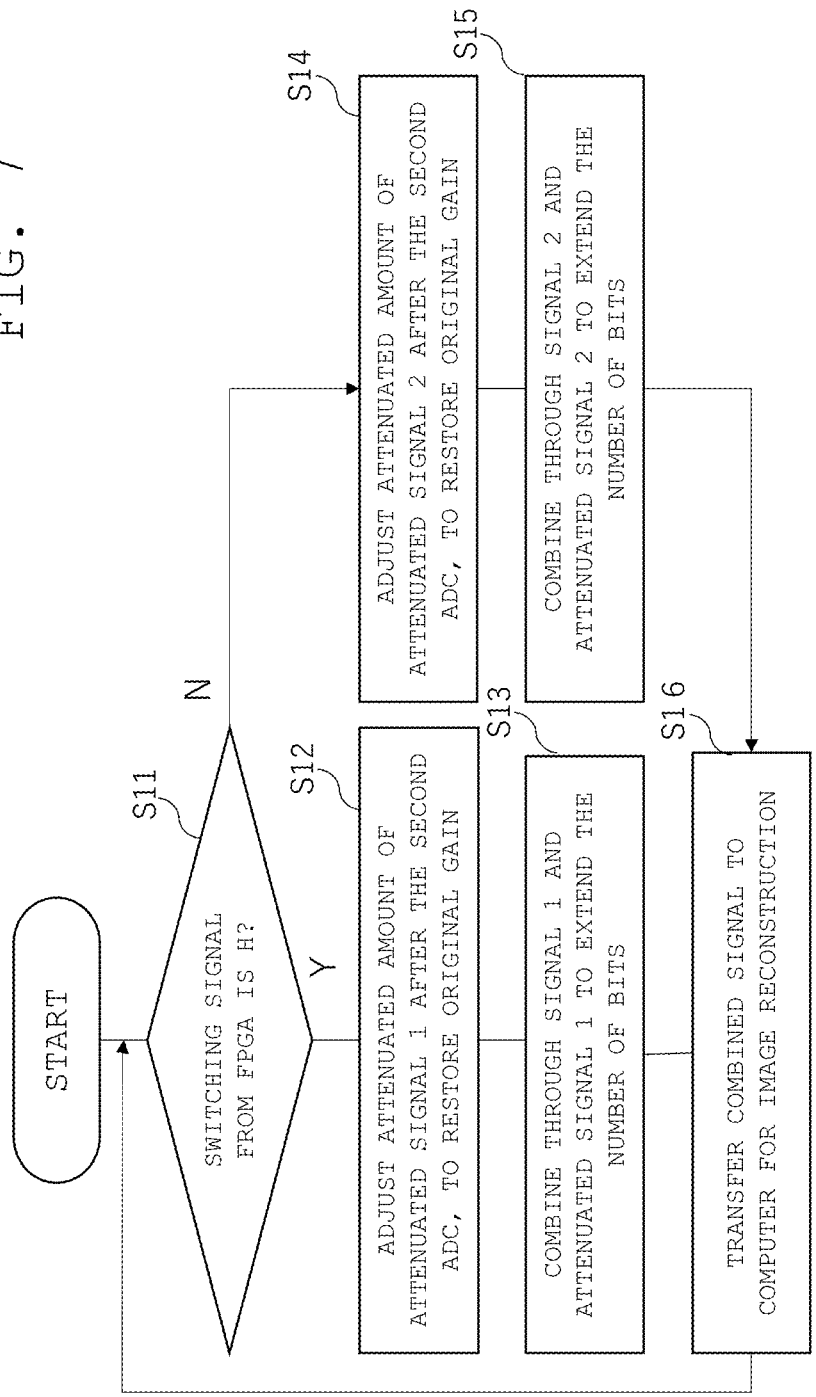
FIG. 7 is a flowchart showing a data processing after ADC according to the first embodiment.

As shown in the flowchart of FIG. 7, when H (High) is outputted as the switching signal to the switches (S11), for example, in the processing circuit 206, the digital amplifier 2061 adjusts the attenuation amount of the attenuated signal 1 after the A/D conversion by the second ADC 205 to restore the original gain (S12). With the same timing, the signal combiner 2062 combines the through signal 1 inputted to the processing circuit 206, with the attenuated signal 1 after the attenuation amount is adjusted (S13).

When L (Low) is outputted as the switching signal to the switches (S11), for example, the digital amplifier 2061 adjusts the attenuation of the attenuated signal 2 after the A/D conversion by the second ADC 205 to restore the original gain (S14). With the same timing, the signal combiner 2062 combines the through signal 2 inputted to the processing unit 206 with the attenuated signal 2 after the attenuation amount is adjusted (S15). The receiver 200 transfers thus digitized signals to the computer 300 for image reconstruction (S16).

Figure 8:
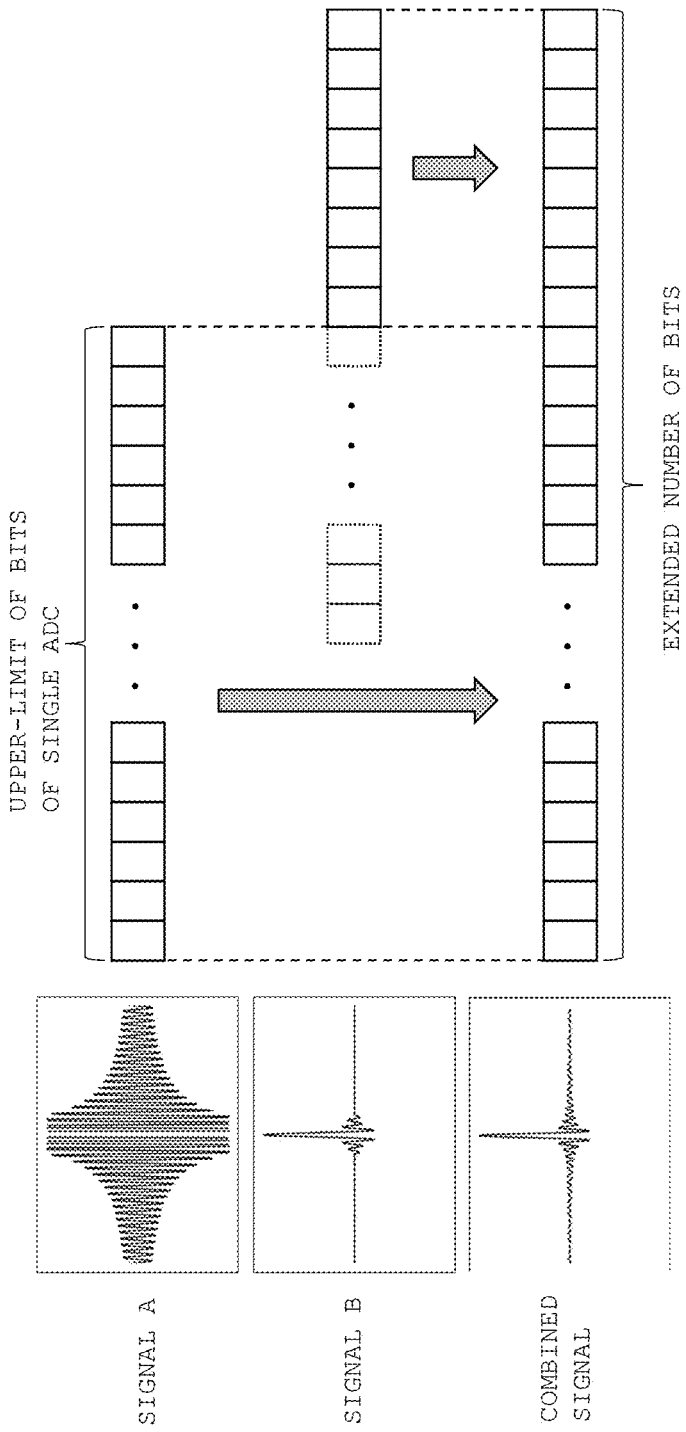
FIG. 8 illustrates extension of a dynamic range by increasing the number of bits according to the first embodiment.

By the gain adjustment and signal combining in the digital signal processing, each of the echo signal 1 and the echo signal 2 becomes a digital signal with the extended number of bits. With reference to FIG. 8, there will be described the extension of the number of bits.

In FIG. 8, the signals A and B correspond to the through signal and the attenuated signal, respectively. As described above, the dynamic range of the echo signal (MR signal) measured by the receiver 200 is wide, but the dynamic range is narrowed because there is an upper limit to the number of bits of one ADC. Eventually, there is obtained the signal whose high intensity part is cut out (overflowed), for example, as in the case of the signal A, if no action is taken (that is, the through signal). On the other hand, in the attenuated signal, the signal intensity has been attenuated, for example, as in the case of the signal B, the signal is compressed to a width that allows to be processed by the number of bits of the ADC, and thus this signal can include the part overflowed from the signal A. It should be noted, however, the fine part of the signal B is smoothed.

As shown in the right side of FIG. 8, when the signal A and the signal B are digitized by the ADC having the same upper limit to the number of bits, the bits are allocated to the fine part of the signal having the wide dynamic range (signal A), and for the overflowed portion, the bits are allocated to the attenuated signal (signal B). In the combined signal, the number of bits is substantially extended. Since the increase in the number of bits results in an increase in the dynamic range, the combined signal of the signal A and the signal B becomes a digital signal in which the dynamic range is virtually extended.

The extended dynamic range DR can be calculated by the following equation:

$$DR = 6.02N + 1.76 + 10_{log10}(f_s/2BW)$$

where N is the upper-limit of bits of the ADC to be used, $f_s$[Hz] is the sampling frequency, and BW[Hz] is the bandwidth. For example, when N is 14 bits, fs is 40 MHz, and BW is 1 kHz, DR becomes 127.3 dB according to the above equation. Then, if N is virtually extended to 20 bits, DR becomes 163.4 dB when the other conditions are equivalent, and it is calculated that extension of 36.1 dB is possible.

As described above, as for the signal having a wide dynamic range peculiar to MR signals, the processing circuit 206 treats the fine part of the signal as the through signal, and assigns bits of the attenuated signal after gain adjustment to the overflowed part, thereby enabling highly accurate A/D conversion to all sampling points.

The receiver 200 transfers the digitized signal as described above to the computer 300 for image reconstruction. Processing steps such as the image reconstruction in the computer 300 are the same as those of the conventional MRI apparatus, and detailed description of the processing will not be provided here.

As described so far, according to the present embodiment, even a signal having a wide dynamic range that is difficult to process with a normal ADC can be processed by dividing the signal into two systems; a signal part of fine variation and a signal part of overflowing, thereby increasing the upper limit of the number of bits that has been limited in a single ADC, and extending the dynamic range. In addition, the receiver 200 divides each of the multiple (two in FIG. 4) input echo signals into two-system signals, and performs the A/D conversion on the divided signals with respect to each system by switching. Therefore, it is possible to extend the dynamic range without increasing the number of ADCs unlike the prior art.

Modification of the First Embodiment

In the first embodiment, there has been described the case where two echo signals are inputted simultaneously to the receiver 200. It is further possible for the receiver 200 to process three or more signals, considering the switching speed and the sampling speed of the switch 203. Processing of three or more signals may be performed, for example, in the case of using a multi-array coil comprising three or more small receive coils, or in the case of processing each complex signal of two or more receive coils.

Figure 9:
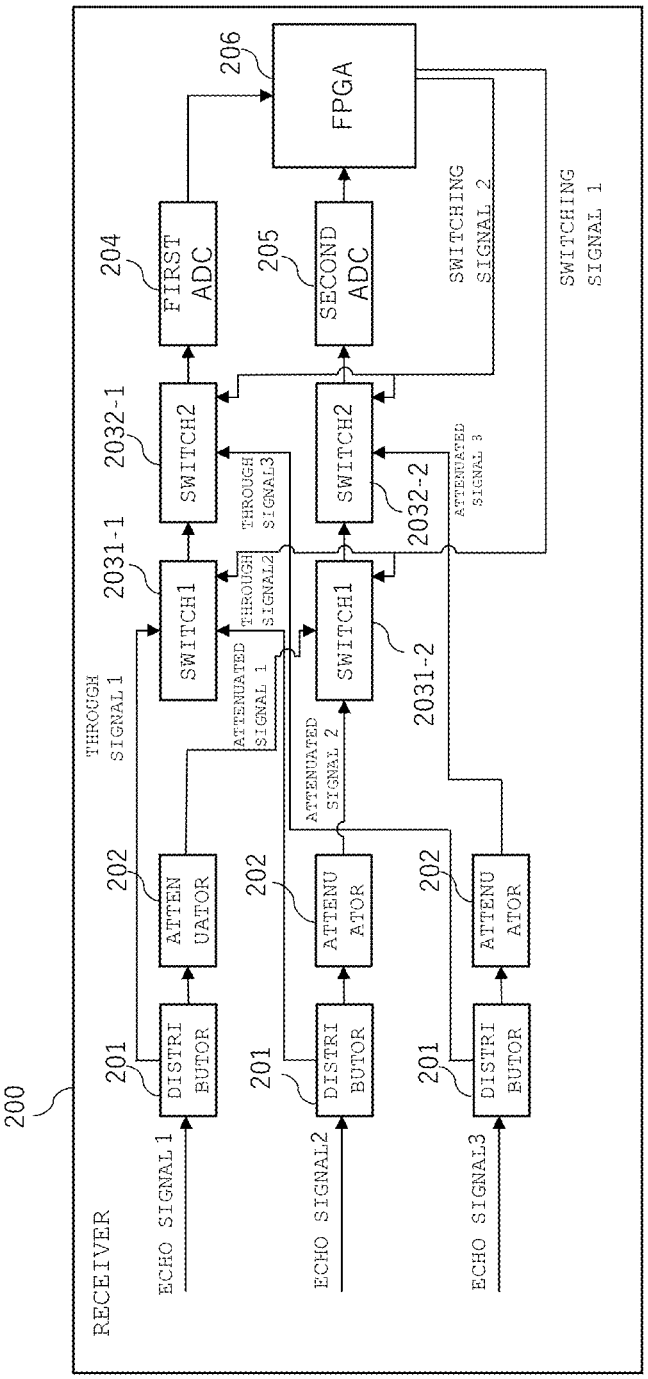
FIG. 9 illustrates a first modification of the receiver according to the first embodiment.

FIG. 9 illustrates a configuration example (first modification) of the receiver 200 in the case of processing three signals. In FIG. 9, circuits having the same function are denoted by the same reference numeral, and "−1" or "−2" is added to the end when distinguishing them from each other. As illustrated, the receiver 200 comprises as many distributors 201 as the number M of the signals to be processed (M=3 in the figure). Two-stage switches 2031 and 2032 (two switches respectively) are provided for switching the inputs to the ADCs. The switch 2031 in the first stage is switched by the switching signal 1 emitted from the processing circuit 206, and the switch 2032 in the second stage is switched by the switching signal 2.

As in the first embodiment, the distributor 201 divides the input signals into the same number as the number of signals to be processed, sets one output as the through signal, and sends the other output to the attenuator 202. Then, each of the echo signals becomes the through signal and the attenuated signal. As in the first embodiment, the through signals of the echo signal 1 and of the echo signal 2 are inputted to the first-stage switch 2031-1, and the attenuated signals of the echo signal 1 and of the echo signal 2 are inputted to the first-stage switch 2031-2. The outputs from the first-stage switches 2031-1 and 2031-2 are inputted to the second-stage switches 2032-1 and 2032-2, respectively. At the same time, the through signal of the echo signal 3 is inputted to the second-stage switch 2032-1 and the attenuated signal of the echo signal 3 is inputted to the second-stage switch 2032-2.

Figure 10:
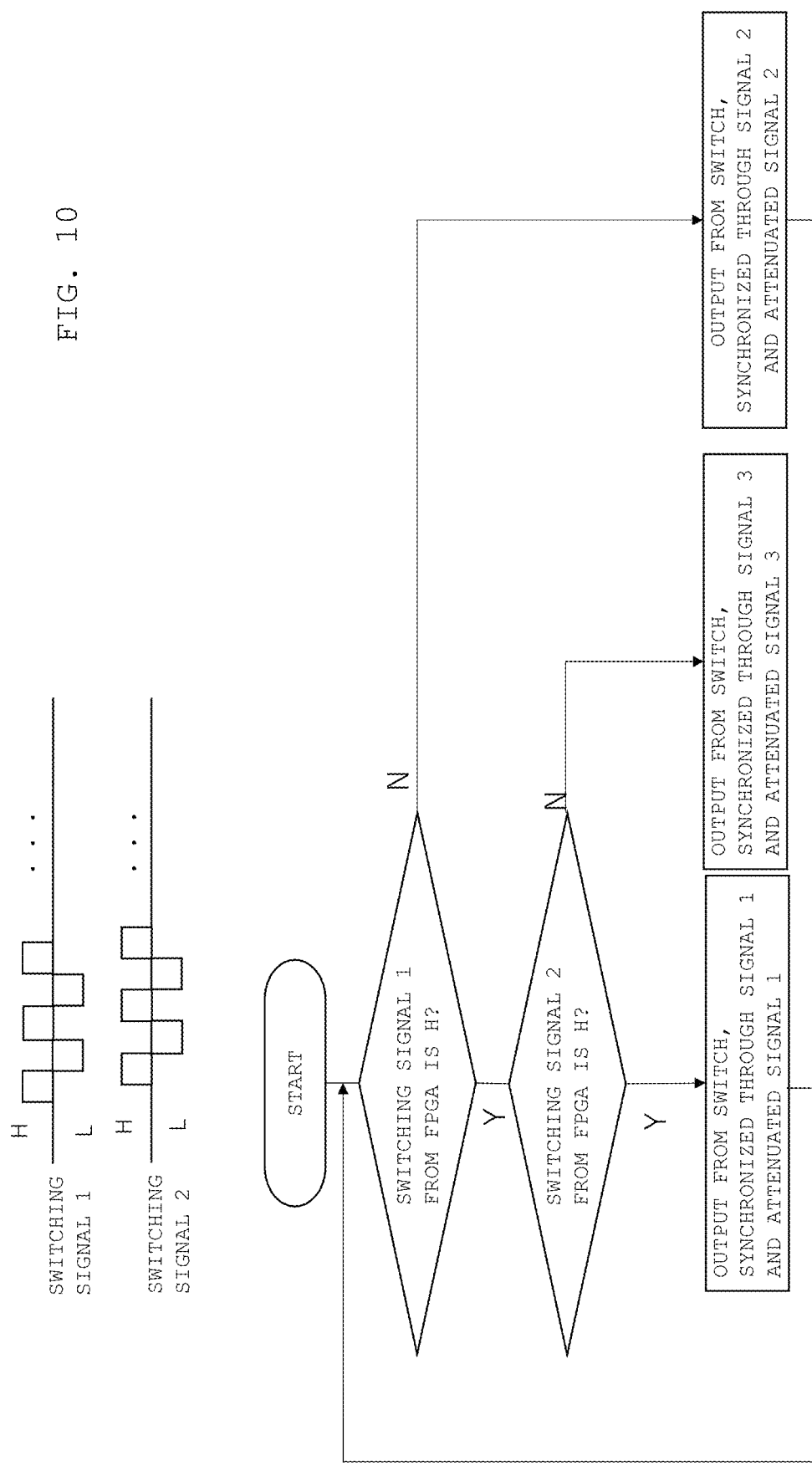
FIG. 10 is a flowchart showing an operation of the switch according to the first modification.

The switching signals 1 and 2 are switched at the timing as shown in the upper side of FIG. 10, for example. Consequently, as shown in the lower side of FIG. 10, when the switching signals 1 and 2 entering the switches 2031 and 2032 respectively are both H, the through signal and the attenuated signal of the echo signal 1 are synchronously inputted to the first ADC 204 and the second ADC 205, respectively. When the switching signal 1 is H and the switching signal 2 is L, the through signal and the attenuated signal of the echo signal 3 are synchronously inputted to the first ADC 204 and the second ADC 205, respectively, via the switch 2032. When the switching signal 1 is L, the switching signal 2 is H, and the through signal and the attenuated signal of the echo signal 2 are synchronously inputted to the first ADC 204 and the second ADC 205 via the switch 2031 and the switch 2032.

In the present modification, the control of the switching signals 1 and 2 differs from that of the first embodiment. However, by installing additional distributors according to the number of the signals, the ADC processing can be performed in the same manner as in the first embodiment, and similar advantages can be obtained.

Figure 11:
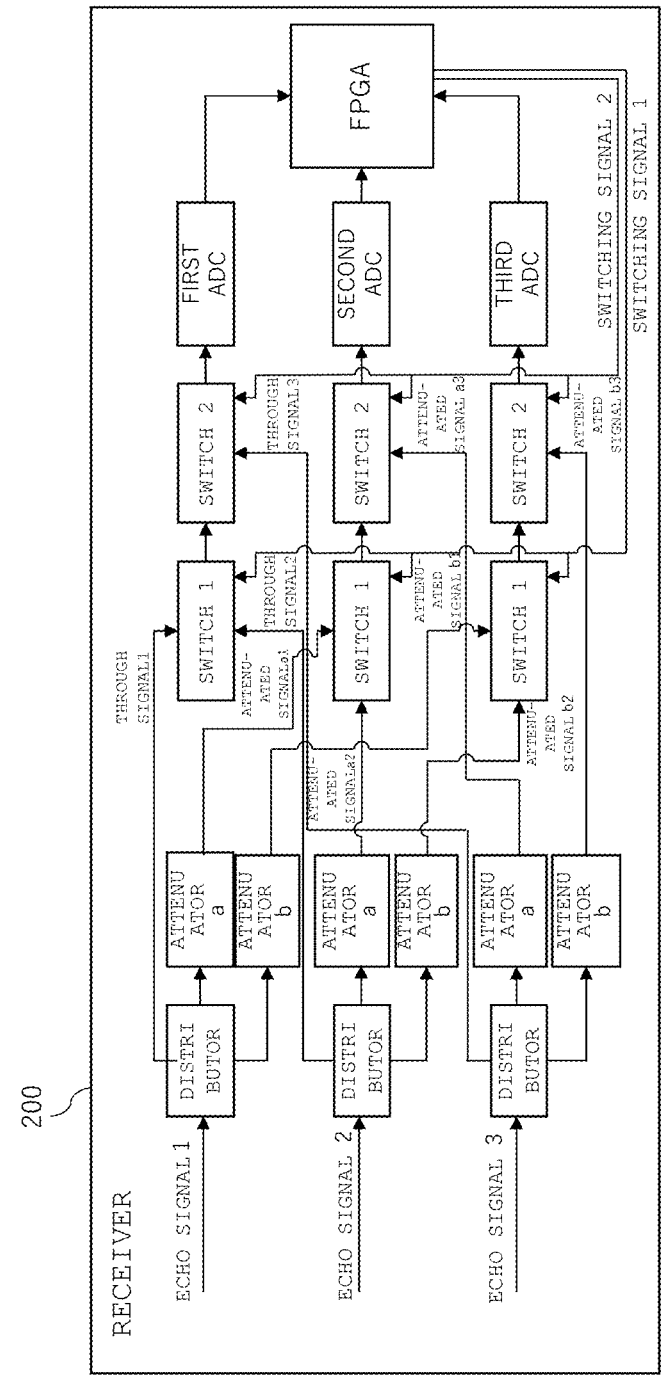
FIG. 11 illustrates a second modification of the receiver of the first embodiment.

FIG. 11 shows another modification (second modification) in the case where the number of signals is three or more. In this modification, the number of signals distributed from the distributor 201 is increased. One output is the through signal, and the other two outputs are respectively attenuated by two attenuators (attenuator a and attenuator b). Three ADCs are provided respectively in association with one through signal and the signals attenuated by the two attenuators (attenuated signal a and attenuated signal b), and two-stage switches are arranged respectively in the preceding stages of the three ADCs.

In the switches 1 of the first stage (three switches 1), there are inputted respectively, the through signals, the attenuated signals a, and the attenuated signals b of the echo signals 1 and 2. In the switches 2 of the second stage (three switches 2), there are inputted respectively, the outputs from the switches of the first stage, and the through signal, the attenuated signal a, and the attenuated signal b of the echo signal 3.

Also in this configuration, similarly to the first modification, when the first-stage switch is H and the second-stage switch is H, the three signals divided from the echo signal 1 are respectively inputted to the three ADCs, digitized, and inputted to the processing circuit 206. When the first-stage switch is L and the second-stage switch is H, three signals divided from the echo signal 2 are inputted to the three ADCs, respectively, and when the second-stage switch is L, three signals divided from the echo signal 3 are inputted to the three ADCs, respectively.

In the second modification, the attenuators are additionally installed, thereby enabling obtainment of multiple attenuated signals having different degrees of attenuation according to the dynamic range of the original signal, and it is possible to further extend the dynamic range without increasing the number of ADCs in response to the number of the signals. Alternatively, when the number of bits of the ADC is smaller than that of the first embodiment or the first modification, the number of bits can be increased as in the first embodiment or the first modification.

Second Embodiment

In the first embodiment, one of the divided signals is the through signal and the other is the attenuated signal. In the present embodiment, the gain adjuster adjusts the attenuation amount of each of the divided signals appropriately, so as to optimize the dynamic range.

Also in the present embodiment, the entire configuration of the MRI apparatus is the same as that of the first embodiment shown in FIG. 1. There will now be described the present embodiment focusing on the points different from the first embodiment.

Figure 12:
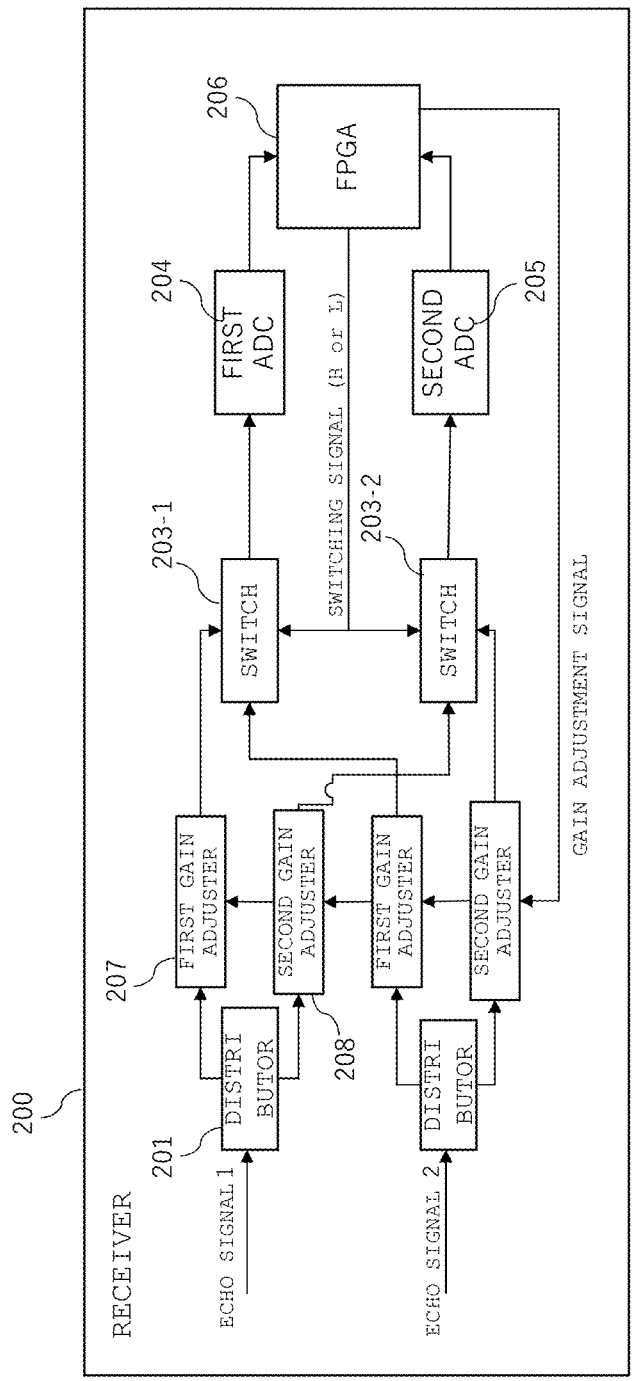
FIG. 12 is a block diagram showing a configuration of the receiver according to the second embodiment of the present invention.

FIG. 12 illustrates a configuration example of the receiver 200 according to the second embodiment. Also in this configuration example, there will be described the case where two echo signals are inputted to the receiver 200, but the echo signals inputted to the receiver 200 are not limited to two.

As illustrated, the receiver 200 of the second embodiment comprises the distributor 201 configured to divide each of multiple input echo signals into two system signals, and a first gain adjuster 207 and a second gain adjuster 208 connected to the output side of the distributor 201. Further, the following configuration is the same as that of the first embodiment, that is, there are provided the first ADC 204 to receive outputs from the two first gain adjusters 207 after switching by the switch 203, and the second ADC 205 to receive outputs from the two second gain adjusters 208 after switching by the switch 203. In addition, it is also the same as the first embodiment that the switching signal from the processing circuit 206 triggers the switching of each switch 203.

As shown in FIG. 13, the processing circuit 206 comprises two gain adjusters 2065 (gain adjuster a and gain adjuster b) configured to restore the gains having been adjusted by the two types of the first gain adjusters 207 and the second gain adjusters 208, and a gain calculation unit 2064 configured to calculate gains of the first and the second gain adjusters 207 and 208 and of the two gain adjusters 2065.

The gain calculation unit 2064 adjusts the values adjusted by the first gain adjuster 207 and the second gain adjuster 208 to optimum adjustment values in accordance with the dynamic range of the original MR signal. The dynamic range of the original MR signal varies depending on the imaging conditions and the imaging target. Thus, for example, the dynamic range can be obtained by using MR signal obtained by the prescan prior to the main scan to acquire an image of the subject, and the adjustment values are calculated based on this obtained dynamic range. Generally, in MRI, the prescan is performed to determine imaging processing conditions and other various conditions prior to the main scan, and thus it is not necessary to perform additional prescan for the gain adjustment, and the prepared prescan measurement signals can be used. Instead of using the prescan data, it is alternatively possible to calculate the adjustment values using the measurement signals obtained during the main scan.

For example, in the case of a signal having an extremely large dynamic range, the adjustment amount is set as the following; i.e., the first gain adjuster 207 decreases the gain to some extent, that is, attenuates the gain by a predetermined amount, and the second gain adjuster 208 attenuates the gain by a larger attenuation amount (an attenuation amount covering the entire signal). To what extent is the gain attenuated depends on the performance of the ADC to be used and the design of the analogue circuitry, and is not limited to a specific amount. The first gain adjuster 207, however, may attenuate the gain to an amount that can cover up to about ⅓ of the signal intensity, for example. It is further possible that the adjustment value by the first gain adjuster 207 is zero, that is, the output from the first gain adjuster 207 is a through signal, and only the second gain adjuster 208 performs the gain adjustment. In the case where the gain adjustment by the second gain adjuster 208 corresponds to the signal attenuation, the adjustment is the same as that in the first embodiment. In addition, it is also possible to make the adjustment for increasing the gain, though there are few cases in which the gain adjusters 207 and 208 increase the gain (amplify the signal). For example, in the case where the dynamic range of the original MR signal is small and there is no signal that overflows without any gain adjustment, that is, the MR signal can be processed by the provided ADC, there is a possibility that one of the gain adjusters does not make the adjustment, but the other gain adjuster makes the adjustment to increase the gain.

The adjustment values of the two first gain adjusters 207 respectively associated with the two input echo signals, may be basically the same, and the two second gain adjusters 208 respectively associated with the two input echo signals may be the same. However, they may vary in accordance with the echo signals inputted to the receiver 200. For example, the dynamic range of the MR signal may vary depending on the channel of the receiver, and in such cases, the signal for each channel may be adjusted differently.

The following processing steps are the same as in the first embodiment; that is, the outputs from the gain adjusters of the two systems (the two first gain adjusters 207 and the two second gain adjusters 208) are inputted to the switches 203-1 and 203-2, respectively, one of the outputs from the first gain adjusters is processed by the first ADC 204 and one of the outputs from the second gain adjusters is processed by the second ADC 205, after the switch 203 is switched by the signal from the processing circuit 206, and then, the outputs from the ADCs are combined after the gain readjustment in the processing circuit 206.

Although the present embodiment has been described with reference to the case where two signals are inputted to the receiver 200, the present embodiment is also capable of performing a plurality (three or more) of signal processing as described in the modification of the first embodiment.

According to the present embodiment, it is possible to flexibly respond to the MR signals actually measured, and as in the first embodiment, it is not necessary to increase the ADCs more than the number of signals inputted to the receiver 200, further enabling highly accurate A/D conversion capable of coping with a signal having a wide dynamic range.

What is claimed is:
1. A magnetic resonance imaging apparatus comprising
a magnetic field generator configured to generate nuclear magnetic resonance in a subject,
a receiver having a receive coil configured to receive a nuclear magnetic resonance signal emitted from the subject, and
an arithmetic unit configured to perform a process including image reconstruction using the nuclear magnetic resonance signals received by the receiver, wherein
the receiver comprises
a distributor configured to divide the nuclear magnetic resonance signal into at least two-system signals; a first-system signal and a second-system signal,
a gain adjuster configured to perform gain adjustment on at least one of the first-system signal and the second-system signal,
a first AD converter configured to perform analog-to-digital conversion on the first-system signal and a second AD converter configured to perform analog-to-digital conversion on the second-system signal, the first-system signal and the second-system signal having been adjusted by the gain adjuster to have different gains, and
a digital processor configured to restore the gain of the digitized signal after adjusted by the gain adjuster, to an original gain, and to combine the digitized two-system signals, wherein
the digital processor further comprises a control unit configured to control inputs to the first AD converter and to the second AD converter and the outputs from the first AD converter and from the second AD converter.

2. The magnetic resonance imaging apparatus according to claim 1, wherein
the number of the nuclear magnetic resonance signals inputted to the receiver is more than one, and
the control unit performs control with respect to each of the nuclear magnetic resonance signals in such a manner that the inputs to the first AD converter and to the second AD converter are performed with the same timing, and the outputs from the first AD converter and from the second AD converter are performed with the same timing.

3. The magnetic resonance imaging apparatus according to claim 1, wherein
the first-system signal is directly inputted to the first AD converter, and the second-system signal is subjected to gain adjustment by the gain adjuster, and then inputted to the second AD converter.

4. The magnetic resonance imaging apparatus according to claim 1, wherein
the receiver receives multiple nuclear magnetic resonance signals, and as the distributor, multiple distributors are provided respectively in association with the multiple nuclear magnetic resonance signals, and
switches are provided respectively, between an output from each distributor and the first AD converter and between the other output from the distributor and the second AD converter, and by switching in the switches, the first-system signals are switched therebetween and the second-system signals are switched therebetween with respect to each of the nuclear magnetic resonance signals, and the switched signals are subjected to analog-to-digital conversion.

5. The magnetic resonance imaging apparatus according to claim 2, wherein
the multiple nuclear magnetic resonance signals are complex signals.

6. The magnetic resonance imaging apparatus according to claim 2, wherein
the receive coil is a multi-channel receive coil having multiple small receive coils, and the multiple nuclear magnetic resonance signals are received respectively by the multiple small receive coils.

7. The magnetic resonance imaging apparatus according to claim 1, wherein
the gain adjuster is an attenuator.

8. The magnetic resonance imaging apparatus according to claim 1, wherein
the digital processor further comprises a gain calculator configured to calculate an amount of the gain adjustment performed by the gain adjuster.

9. The magnetic resonance imaging apparatus according to claim 8, wherein
the gain calculator calculates the amount of the gain adjustment, using the nuclear magnetic resonance signals acquired during a prescan or during imaging.

10. A signal processing method that processes a nuclear magnetic resonance signal measured by a magnetic resonance imaging apparatus, comprising
dividing the nuclear magnetic resonance signal into two-system signals; a first-system signal and a second-system signal, performing analog-to-digital conversion on the first-system signal as it is or after gain adjustment, performing analog-to-digital conversion on the second-system signal after the gain adjustment to have a gain different from that of the first-system signal, and after restoring the adjusted gain to an original gain, combining the digitized first-system signal with the digitized second-system signal, wherein
the signal processing method controls switching the analog-to-digital conversion in response to the number of nuclear magnetic resonance signals to be processed, along with synchronizing the timing of the analog-to-digital conversion of the first-system signal with the timing of the analog-to-digital conversion of the second-system signal, with respect to one nuclear magnetic resonance signal.

* * * * *